United States Patent [19]
Ponceblanc et al.

[11] Patent Number: 5,847,223
[45] Date of Patent: Dec. 8, 1998

[54] PROCESS FOR THE PREPARATION OF METHYL MERCAPTAN

[75] Inventors: Hervé Ponceblanc, Paris; François Tamburro, Lyons, both of France

[73] Assignee: Rhone-Poulenc Nutrition Animale, Antony, France

[21] Appl. No.: 667,545

[22] Filed: Jun. 21, 1996

[30] Foreign Application Priority Data

Jun. 23, 1995 [FR] France .................................. 95 07571

[51] Int. Cl.$^6$ ................................................. C07C 319/00
[52] U.S. Cl. ............................................................. 568/71
[58] Field of Search ................................................. 568/71

[56] References Cited

FOREIGN PATENT DOCUMENTS

A-1161066  8/1958  France .
A-2477538  9/1981  France .

OTHER PUBLICATIONS

English language Derwent Abstract of FR–A–2477538. 1981.

Kudenkov et al., "Synthesis of Methylmercaptan in the Presence of Base Catalysts," Reaction Kinetics and Catalysis Letters, 38(1):199–203 (1989).

Translation of the "Resume" (Abstract) of FR–A–1161066. 1958.

*Primary Examiner*—Samuel Barts
*Attorney, Agent, or Firm*—Finnegan, Henderson, Farabow, Garrett & Dunner, L.L.P.

[57] ABSTRACT

A process for the preparation of methyl mercaptan which comprises reacting methanol and hydrogen sulphide in the vapor phase in the presence of a catalyst, wherein the catalyst is an alkali metal carbonate deposited on alumina, and wherein the reaction is carried out at a temperature below 350° C.

11 Claims, No Drawings

PROCESS FOR THE PREPARATION OF METHYL MERCAPTAN

The present invention relates to an improved process for the preparation of methyl mercaptan. The invention relates more particularly to a process for the preparation of methyl mercaptan from methanol and hydrogen sulphide. The invention also relates to catalysts that are useful in this preparation and that have improved stability.

The preparation of methyl mercaptan from methanol and hydrogen sulphide has been known for a considerable time. A description of this type of reaction was given, for example, by Sabatier and Mailhe in 1910 in a Science Academy Report 150 823–6, 1569–72 and 1217–21.

The reaction is described as taking place in the presence of various catalysts based particularly on alumina optionally doped with various metals, among which mention may be made of alkali metals, alkaline-earth metals, cadmium sulphide, antimony sulphide, tin oxide, phosphotungstic acid, phosphomolybdic acid and potassium tungstate.

The reaction proceeds in a single reactor or in several successive reactors. Thus, according to GB patent 1,417, 532, the disclosure of which is incorporated herein by reference, it is known to prepare methyl mercaptan by reaction of methanol and hydrogen sulphide in a molar ratio of hydrogen sulphide to methanol of between 1.10:1 and 2.5:1, in a series of at least three catalytic reactors. The catalyst employed is preferably an alumina doped with potassium tungstate, the reaction temperature being maintained between 320° and 370° C.

The reaction side products in this type of process include dimethyl sulphide and carbon dioxide. The formation of dimethyl sulphide increases with the reaction temperature, but the degree of conversion of the methanol also increases with the temperature, and hence an equilibrium must be found between the formation of dimethyl sulphide and the conversion of the starting methanol.

It is also known, from the articles of the Russian authors Kudenov, Paukshtis and Mashkina, published in React. Kinet. Catal. Lett., Vol. 38, No. 1, 199–203 (1989), to use, as reaction catalysts, aluminas doped with potassium tungstate, with potassium carbonate, with potassium hydroxide or with sodium hydroxide, at temperatures of between 360° and 450° C. The best selectivity towards methyl mercaptan is obtained using potassium tungstate either at 360° or at 400° C. The best degree of methanol conversion is obtained when the temperature is highest, that is to say at 500° C. If the yield of methyl mercaptan is calculated as a function of the temperature and of the type of catalyst used, one would be inclined to use a temperature of between 400° and 450° C. without distinction as regards the type of catalyst.

According to another article from the same authors, published in Kinetika i Kataliz, Vol. 29, No. 5, pp. 1174–1180, September–October 1988 and which compares the activity and selectivity of alumina-based catalysts doped with potassium tungstate or with potassium carbonate, it was observed that at a temperature of 360° C. the selectivity towards methyl mercaptan was the same regardless of whether a catalyst doped with the tungstate or with the carbonate was used.

The present invention is based on the entirely surprising appreciation that the activity and selectivity towards methyl mercaptan of these two types of catalyst are quite different when they are used at temperatures lower than that previously used in the art.

Accordingly, the present invention provides a process for the preparation of methyl mercaptan that comprises reacting methanol and hydrogen sulphide in the vapor phase in the presence of a catalyst, wherein the catalyst is an alkali metal carbonate deposited on alumina, and wherein the reaction takes place at a temperature below 350° C. (i.e., not exceeding 350° C.).

The alkali metal carbonate used is preferably chosen from sodium, potassium and caesium carbonates; potassium carbonate is more preferred. The amount by weight of alkali metal carbonate deposited on the alumina varies as a function of the nature of the alkali metal, but will preferably range from 2 to 20% by weight. When potassium carbonate is used, the amount deposited on the alumina will preferably range from 2 to 10% by weight, and will more preferably be about 6.4% by weight.

The reaction temperature preferably ranges from 230° to 330° C. and more preferably ranges from 280° to 310° C. The reaction temperature is the temperature measured at the reactor inlet. The inlet temperature is generally below the outlet temperature, since the reaction is exothermic.

The reaction pressure preferably ranges from 8 to 15 bar (8 to $15 \times 10^5$ pascals).

The catalyst is preferably distributed in a catalyst system comprising at least three reactors.

In a first reactor, also referred to as the converter, preferably all of the hydrogen sulphide is introduced, the methanol being introduced sequentially into each of the other reactors. The overall molar ratio of hydrogen sulphide introduced to methanol introduced preferably ranges from 1.5:1 to 2.5:1. The catalyst used in the converter is preferably alumina. Its role is essentially to convert recycled dimethyl sulphide (originating from the last reactor), in the presence of fresh hydrogen sulphide, into methyl mercaptan.

At the converter outlet, the gases produced are introduced into a reactor that is, at the same time, supplied with methanol. The methanol is introduced partly in liquid form and partly in gaseous form so as to stabilize the reactor temperature. The reason for this is that vaporization of the methanol makes it possible to consume some of the heat produced by the exothermic reaction. The charge of methanol entering, methanol originating from the preceding reactor, and fresh methanol introduced is increasingly large in each of the reactors as the reaction progresses. For each of the reactors, the molar ratio of the hydrogen sulphide to the partial supply of methanol gradually lowers as the reaction progresses, and preferably ranges from 15:1 to 3:1.

The overall ratio of the hydrogen sulphide to the methanol is always within the limits previously indicated. These values make it possible to obtain a high selectivity towards methyl mercaptan to the detriment of the formation of dimethyl sulphide.

After the last reactor, the reaction mixture is introduced into a finisher containing the same catalyst as the preceding series of reactors, but in an equal or larger volume. At the finisher outlet, the reaction gases, consisting of methyl mercaptan, dimethyl sulphide, methanol and hydrogen sulphide and various gases, are separated according to the above-mentioned GB patent 1,417,532.

The invention also relates to catalysts for the preparation of methyl mercaptan which are of improved stability relative to the potassium tungstate-based catalysts known in the prior art. This stability is improved over time.

The following examples illustrate the present invention.

EXAMPLE 1

Preparation of a catalyst of formula $K_2CO_3/Al_2O_3$ at a concentration of 2% by weight, equivalent to an alkali metal cation number of 28.9 mmol/100 g of catalyst.

A 120 ml solution was prepared by dissolving 4.08 g of $K_2CO_3$ (sodium-free) in deionized water. The pH of the final solution was 11.66. 200 g of Procalyse Spheralite 505 alumina were dry-impregnated with the above solution. The catalyst thus prepared was activated at 470° C. The catalyst consisted of 2% by weight of $K_2CO_3$.

EXAMPLE 2

Preparation of a catalyst of formula $K_2CO_3/Al_2O_3$ at a concentration of 6.4% by weight, equivalent to an alkali metal cation number of 92.6 mmol/100 g of catalyst.

The catalyst was prepared according to the method described in Example 1, using 13.68 g of $K_2CO_3$ to impregnate 200 g of alumina. The pH of the solution before impregnation was 11.6.

EXAMPLE 3

Preparation of a catalyst of formula $K_2CO_3/Al_2O_3$ at a concentration of 10% by weight, equivalent to an alkali metal cation number of 144.7 mmol/100 g of catalyst.

The catalyst was prepared according to the method described in Example 1, using 22.22 g of $K_2CO_3$ to impregnate 200 g of alumina. The pH of the solution before impregnation was 11.75.

EXAMPLE 4

Preparation of a catalyst of formula $Na_2CO_3/Al_2O_3$ at a concentration of 4.9% by weight, equivalent to an alkali metal cation number of 92.4 mmol/100 g of catalyst.

The catalyst was prepared according to the method described in Example 1, using 10 g of $Na_2CO_3$ to impregnate 200 g of alumina. The pH of the solution before impregnation was 10.79.

EXAMPLE 5

Preparation of a catalyst of formula $Cs_2CO_3/Al_2O_3$ at a concentration of 15.1% by weight, equivalent to an alkali metal cation number of 92.5 mmol/100 g of catalyst.

The catalyst was prepared according to the method described in Example 1, using 35.49 g of $Cs_2CO_3$ to impregnate 200 g of alumina. The pH of the solution before impregnation was 11.02.

COMPARATIVE EXAMPLE 1

This catalyst consisted of alumina alone.

The catalyst of Comparative Example 1 consisted of non-impregnated Spheralite 505 alumina reheated according to the same procedure as in Example 1.

COMPARATIVE EXAMPLE 2

Preparation of a catalyst of formula $K_2WO_4/Al_2O_3$ at a concentration of 14% by weight, equivalent to an alkali metal cation number of 92.5 mmol/100 g of catalyst.

The catalyst was prepared according to the method described in Example 1, using 40.23 g of $K_2WO_4$ —$2H_2O$ to impregnate 200 g of alumina. The pH of the solution before impregnation was 11.

COMPARATIVE EXAMPLE 3

Preparation of a catalyst of formula $Na_2WO_4/Al_2O_3$ at a concentration of 13.6% by weight, equivalent to an alkali metal cation number of 92.5 mmol/100 g of catalyst.

The catalyst was prepared according to the method described in Example 1, using 36 g of $Na_2WO_4$ —$2H_2O$ to impregnate 200 g of alumina. The pH of the solution before impregnation was 9.88.

EXAMPLE 6

Catalytic test of the catalysts of Examples 1 to 5 and Comparative Examples 1 to 3.

The catalytic performance of the catalysts described in Examples 1 to 5 and Comparative Examples 1 to 3 were determined under the following conditions.

A 90 ml bed, consisting of catalyst in the form of beads having an undiluted diameter of about 3 mm, was contained in a reactor 35 cm in height and 27.3 mm in inside diameter.

The reactor inlet gases consisted of a mixture of methanol, hydrogen sulphide, methyl mercaptan, dimethyl sulphide and water in the following molar proportions: 6.5/70.5/11.5/4/7.5%. The gases were first passed through a bed of 100 ml of corundum beads for preheating to the reaction temperature. The pressure in the reactor was maintained at 10 bar. The reaction temperature was maintained at 320° C.

The HVV or hourly volume velocity, calculated under standard temperature and pressure conditions, was 6667 $h^{-1}$, i.e. a contact time of 0.54 s.

The hourly volume velocity, HVV, is defined as the ratio:

$$\frac{\text{Total flow rate of the reactants under standard conditions}}{\text{volume of catalyst}}$$

The degree of conversion of the methanol, $Xg$, is defined as the ratio:

$$\frac{\text{Number of moles of menthanol converted}}{\text{Number of moles of methanol converted}} \times 100$$

The selectivity towards product i, $Si$, is defined as the ratio:

$$\frac{\text{Number of moles of product } i \text{ formed}}{\text{Number of moles of menthanol converted}} \times 100$$

The yield of product i, $Yi$, is defined as the product $Xg \times Si$.

The performance of the catalysts of Examples 1 to 5 and Comparative Examples 1 to 3, measured after 100 hours under reactants, is reported in Table 1 below. MSH stands for methyl mercaptan. DMS stands for dimethyl sulfide.

TABLE 1

| Example | Catalyst (% by weight) | Xg (%) | SMSH (%) | SDMS (%) | $SCO_2$ (%) | YMSH (%) | YDMS (%) |
|---|---|---|---|---|---|---|---|
| C1 | alumina alone | 100 | 60 | 40 | 0 | 60 | 40 |
| 1 | 2% $K_2CO_3$ | 94.0 | 82.5 | 17.5 | 0 | 77.6 | 16.5 |
| 2 | 6.4% $K_2CO_3$ | 93.6 | 93.0 | 5.0 | 2.0 | 86.5 | 4.7 |
| 3 | 10% $K_2CO_3$ | 78.5 | 89.5 | 9.5 | 1.0 | 70.3 | 7.5 |
| 4 | 4.9% $Na_2CO_3$ | 87.0 | 89.0 | 10.0 | 1.0 | 77.4 | 8.7 |
| 5 | 15.1% $Cs_2CO_3$ | 92.0 | 94.0 | 5.0 | 1.0 | 86.5 | 11.0 |
| C2 | 14% $K_2WO_4$ | 75.0 | 94.0 | 4.0 | 2.0 | 70.5 | 3.0 |
| C3 | 13.6 $Na_2WO_4$ | 86.0 | 87.0 | 5.0 | 8.0 | 74.8 | 4.3 |

The methanol conversions and yields of MSH, using the catalysts of Examples 1 to 4 and Comparative Examples 1 and 2, measured at different operating temperatures for a reaction temperature of 370° C. (conditions of accelerated ageing) are reported in Table 2 below:

TABLE 2

| Example | Catalyst (% by weight) | Duration in hours | Xg (%) | YMSH (%) | $-Xg/\Delta t$ (%) for 100 h |
|---|---|---|---|---|---|
| C1 | alumina alone | 100 | 100 | 70.0 | 0 |
|  |  | 150 | 100 | 63.0 |  |
|  |  | 250 | 100 | 62.0 |  |
|  |  | 400 | 100 | 57.0 |  |
| 1 | 2% $K_2CO_3$ | 100 | 100 | 79.0 | 1 |
|  |  | 150 | 100 | 77.5 |  |
|  |  | 250 | 98.0 | 77.0 |  |
|  |  | 400 | 97.0 | 75.0 |  |
| 2 | 6.4% $K_2CO_3$ | 100 | 98.0 | 86.0 | 0.6 |
|  |  | 250 | 98.0 | 86.5 |  |
|  |  | 400 | 97.5 | 87.0 |  |
|  |  | 500 | 96.0 | 87.6 |  |
|  |  | 600 | 95.0 | 87.5 |  |
| 3 | 10% $K_2CO_3$ | 100 | 95.0 | 77.0 | 1.6 |
|  |  | 250 | 93.0 | 77.5 |  |
|  |  | 400 | 91.0 | 78.0 |  |
|  |  | 500 | 88.0 | 77.0 |  |
|  |  | 600 | 87.0 | 75.0 |  |
| 4 | 4.9% $Na_2CO_3$ | 250 | 100 | 88.0 | 1.4 |
|  |  | 400 | 97.5 | 86.0 |  |
|  |  | 500 | 97.0 | 87.0 |  |
|  |  | 600 | 95.0 | 86.0 |  |
| C2 | 14% $K_2WO_4$ | 250 | 90.0 | 85.0 | 5 |
|  |  | 400 | 85.0 | 82.0 |  |
|  |  | 500 | 77.0 | 78.5 |  |
|  |  | 550 | 75.0 | 77.0 |  |

EXAMPLES 6 TO 10 AND COMPARATIVE EXAMPLES 4 TO 8

An industrial test was performed on an array of 7 reactors preceded by a converter. The converter was charged with Spheralite 505® alumina. The 7 reactors were charged either with the catalyst of Example 2 containing 6.4% $K_2CO_3$ or with the catalyst of Comparative Example 2. 5000 kg/h of a mixture containing, by weight:

84% hydrogen sulphide

6% methanol

5% dimethyl sulphide

5% methyl mercaptan was introduced into the converter.

300 kg/h of methanol were introduced into each of the 7 reactors. Several tests were performed at different inlet temperatures of the gases into the reactor. The results are shown in Table 3 below:

TABLE 3

| Example | Temperature (°C.) | Catalyst | Xg | SMSH (%) | SDMS (%) | YMSH (%) |
|---|---|---|---|---|---|---|
| 6 | 230 | 6.4% $K_2CO_3$ | 63.68 | 99.40 | 0.60 | 63.30 |
| C4 | 230 | 14% $K_2WO_4$ | 42.97 | 99.85 | 0.15 | 42.90 |
| 7 | 280 | 6.4% $K_2CO_3$ | 82.77 | 94.44 | 5.56 | 75.17 |
| C5 | 280 | 14% $K_2WO_4$ | 63.27 | 98.56 | 1.44 | 62.36 |
| 8 | 310 | 6.4% $K_2CO_3$ | 91.93 | 85.54 | 14.46 | 75.64 |
| C6 | 310 | 14% $K_2WO_4$ | 72.89 | 96.13 | 3.87 | 70.07 |
| 9 | 340 | 6.4% $K_2CO_3$ | 99.15 | 66.21 | 33.73 | 65.70 |
| C7 | 340 | 14% $K_2WO_4$ | 82.29 | 90.48 | 9.52 | 74.46 |
| 10 | 370 | 6.4% $K_2CO_3$ | 100.00 | 37.77 | 62.23 | 37.77 |
| C8 | 370 | 14% $K_2WO_4$ | 92.07 | 78.53 | 21.47 | 72.30 |

It is clear from Tables 1 to 3 that if it is desired to obtain a more stable catalyst over time and a better yield of methyl mercaptan, it is very advantageous to use a catalyst based on $K_2CO_3$ at a temperature ranging from 230° to 330° C. and preferably ranging from 280° C. to 310° C.

What is claimed is:

1. A process for preparing methyl mercaptan, which comprises:

reacting methanol with hydrogen sulphide in a vapor phase and in the presence of a catalyst, said catalyst being an alkali metal carbonate deposited on alumina and said reaction being carried out at a temperature at or below 350° C.

2. A process according to claim 1, wherein said alkali metal carbonate is selected from sodium carbonate, potassium carbonate and caesium carbonate.

3. A process according to claim 2, wherein said alkali metal carbonate is potassium carbonate.

4. A process according to claim 1, wherein from 2 to 20% by weight of said alkali metal carbonate is deposited on said alumina.

5. A process according to claim 3, wherein from 2 to 10% by weight of said potassium carbonate is deposited on said alumina.

6. A process according to claim 5, wherein about 6.4% by weight of said potassium carbonate is deposited on said alumina.

7. A process according to claim 1, wherein the reaction temperature ranges from 230° to 330° C.

8. A process according to claim 7, wherein the reaction temperature ranges from 280° to 310° C.

9. A process according to claim 1, wherein the molar ratio of hydrogen sulphide to methanol in the reaction ranges from 1:5:1 to 2:5:1.

10. A process according to claim 1, wherein the reaction is carried out at a pressure which ranges from 8 to 15 bar.

11. A process according to claim 1, wherein said catalyst is distributed in a system comprising at least three reactors.

* * * * *